United States Patent [19]

Takenaka et al.

[11] Patent Number: 5,108,558

[45] Date of Patent: Apr. 28, 1992

[54] PROCESS FOR THE ELECTROREDUCTION OF AROMATIC CARBOXYLIC ACIDS

[75] Inventors: Shinji Takenaka; Ryu Oi; Chitoshi Shimakawa, all of Fukuoka, Japan

[73] Assignee: Mitsui Toatsu Chemicals, Incorporated, Tokyo, Japan

[21] Appl. No.: 367,924

[22] Filed: Jun. 19, 1989

[30] Foreign Application Priority Data

Jun. 20, 1988 [JP] Japan .................. 63-150178

[51] Int. Cl.$^5$ .................................. C25B 3/00
[52] U.S. Cl. .................... 204/75; 204/73 R
[58] Field of Search .......... 204/73 R, 75, 76, 77

[56] References Cited

U.S. PATENT DOCUMENTS 4,402,805 9/1983 Donohue .................. 204/75
4,560,450 12/1985 Morduchowitz et al. ....... 204/75
4,684,449 8/1987 Takenaka et al. ........... 204/75

OTHER PUBLICATIONS

Baizer et al., "Organic Electrochemistry An Introduction and a Guide", 2nd ed., Marcel Dekker Inc., New York, 1983, p. 183.

Primary Examiner—John F. Niebling
Assistant Examiner—Steven P. Marquis
Attorney, Agent, or Firm—Millen, White & Zelano

[57] ABSTRACT

Disclosed herein is a process for the electroreduction of aromatic acids comprising reducing an aromatic carboxylic acid electrolytically in an aqueous acidic solution by the use of a material of a low oxygen overvoltage as the anode for oxygen generation, thereby producing the corresponding benzyl alcohol in high yield in a single electrolytic apparatus.

19 Claims, 2 Drawing Sheets

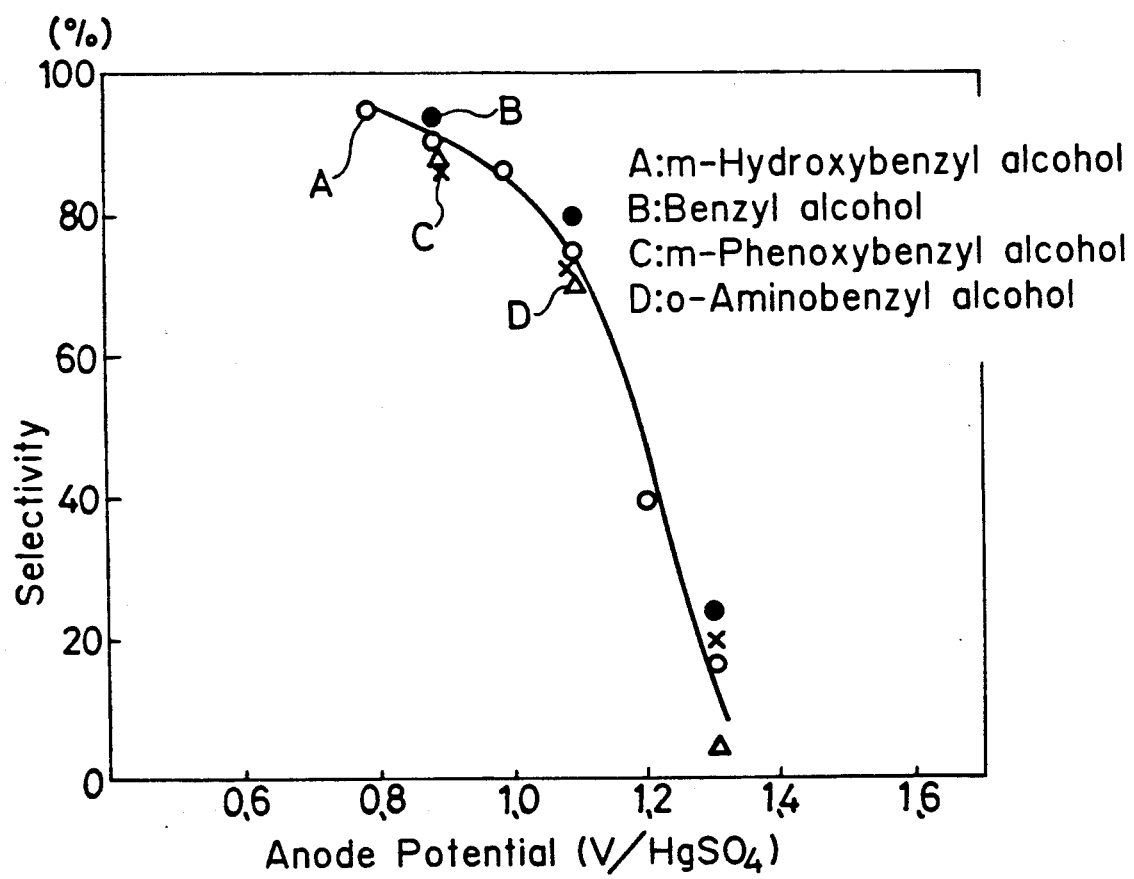

PROCESS FOR THE ELECTROREDUCTION OF AROMATIC CARBOXYLIC ACIDS

BACKGROUND OF THE INVENTION

1. Field of the Invention:

The invention relates to a process for producing benzyl alcohols from the corresponding aromatic carboxylic acids.

Among benzyl alcohols, there are many compounds useful as intermediates for agricultural chemicals and pharmaceuticals or as perfumes. However, it has not been successful to date to produce them at low costs on an industrial scale.

2. Prior Art of the Invention

It is well known to reduce aromatic carboxylic acids electrolytically in aqueous acidic solutions. For instance, it has been proposed to submit aromatic carboxylic acids to electroreduction at 70° C. in the presence of sodium amalgam and 15 wt.% sulfuric acid [Bericht 38, 1752 (1905)]. However, this process gives so low yield that it has not been adopted industrially.

The present inventors have previously proposed to reduce m-hydroxybenzoic acid or esters thereof electrolytically at a pH of 4 or less in an aqueous solution or in a water-soluble organic solvent (Japanese Patent Laid-Open No. 234987/1985).

The inventors have also proposed to use a cation-exchange membrane as a diaphragm and add a quaternary ammonium salt as a supporting electrolyte in the electroreduction (Japanese Patent Laid-Open No. 243293/1985).

The inventors have further proposed an electroreduction process for producing high purity p-xylylene glycol from other benzoic acids than m-hydroxybenzoic acid, for example, from terephthalic acid (Japanese Patent Laid-Open No. 297482/1987).

In addition, the inventors have proposed an electroreduction process of m-phenoxybenzoic acid as a benzoic acid other than m-hydroxybenzoic acid (Japanese Patent Laid-Open Nos. 17188/1988 and 192883/1988).

The electroreduction of these aromatic carboxylic acids are usually carried out in an aqueous acidic solution. No particular restrictions are imposed on the aqueous acidic solution so far as the acidic substance contained therein is inert to the electrolytic reaction at the cathode. Costwise, however, it is generally desirable to use mineral acids, and hence sulfuric acid has been particularly used from the standpoint of material and yield.

Cathode materials used in the electrolytic reaction include those involving high hydrogen overvoltages, specifically, zinc, lead, cadmium, mercury, and the like.

In the opposing anode, it is common to use metallic materials that are not corroded in aqueous sulfuric acid solutions or otherwise do not affect the cathodic reaction adversely even if they are taken into solution as metallic ions. Platinum, lead oxide, lead and lead alloys are being generally used.

However, the foregoing anode materials including platinum, lead oxide, lead and lead alloys have high oxygen overvoltages at usual supply voltages (0.1 A/dm$^2$-100 A/dm$^2$) and therefore their oxidizing abilities are high. Consequently, when the electrolytic reaction of aromatic carboxylic acids is carried out in a single electrolytic cell in which the anode and cathode compartment are not separated from each other, oxidation as well as reduction take place simultaneously, resulting in a significant decrease in the yield of the intended benzyl alcohols.

In order that the oxidation reaction on the surface of the anode is suppressed and the intended product is obtained in a high yield, it has been necessary to conduct the electrolytic reaction in an anode-cathode separated electrolytic cell in which the anode compartment is separated from the cathode compartment by a diaphragm like an ion-exchange membrane, and feed the raw material only to the cathode compartment.

However, use of the anode-cathode separated electrolytic cell in the industrialization of the electrolytic reaction unavoidably increases the power cost due to the resistance of the diaphragm, increases the cost of expendables as the diaphragm, and causes mass transfer from the cathode compartment to the anode compartment during the reaction. The transfer loss leads to a reduction in the yield, while the two solution tanks required for the anode and cathode renders the apparatus complicated. Further, the installation of the diaphragm has imposed a restriction on the shapes of the electrolytic cell and the electrodes.

SUMMARY OF THE INVENTION

An object of the invention is to provide an improved process for the production of benzyl alcohols in high yields from the corresponding aromatic carboxylic acids by their electroreduction in an aqueous acidic solution in a single electrolytic cell in which the anode compartment is not separated from the cathode compartment, without using a processwise complex anode-cathode separated electrolytic cell.

The inventors have made intensive investigations to attain the above object. As a result, it has been found that when the electrolysis is conducted in a single electrolytic cell, in which the anode and cathode compartments are not divided, by lowering its anode potential, the oxidation and decomposition of organic matters (i.e., aromatic carboxylic acids used as the raw material and/or benzyl alcohols which are organic matters or reduction products derived from the raw material, benzaldehydes as an intermediate, radical anion intermediates, etc.) by the anode are suppressed, and the intended corresponding benzyl alcohols can be obtained with high selectivities.

According to the invention, when an aromatic carboxylic acid is reduced electrolytically in an aqueous acidic solution to produce the corresponding benzyl alcohol, use of an anode material involving a low oxygen overvoltage as the anode material for oxygen generation allows the reaction to proceed in a single electrolytic apparatus, in which the anode is not isolated from the cathode by a diaphragm, in a yield as high as in the conventional process in which the compartments are separated from each other by a diaphragm.

When employed industrially, the process proves to be very useful from a practical viewpoint because the electrolysis is effected in a simple single apparatus provided with a diaphragm only in the electrolytic chamber.

BRIEF DESCRIPTION OF THE DRAWINGS

FIG. 3 illustrates the relationship between the anode potential and the benzyl alcohol selectivity in the reaction in a single electrolytic cell for producing benzyl alcohols by the electroreduction of benzoic acids.

DETAILED DESCRIPTION OF PREFERRED EMBODIMENT

Figure 1:
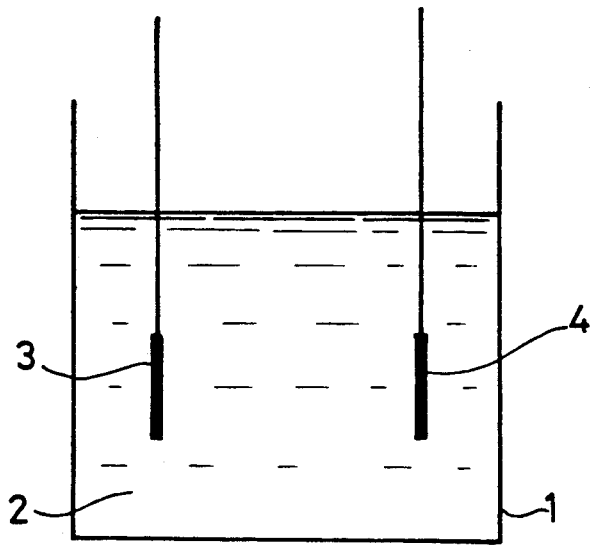
FIG. 1 is a schematic cross section of the beaker-type single electrolytic apparatus of the invention in which no diaphragm is used.

The invention is described in detail hereinbelow. FIG. 3 illustrates the relationship between the anode potential and the benzyl alcohol selectivity in the cathodic reduction of the corresponding benzoic acids in a single electrolytic cell under the control of the anode potential at a fixed level. As clearly seen from FIG. 3, the lower the anode potential, the higher is the benzyl alcohol selectivity. As the anode potential is increased, the selectivity is reduced. At a point where the anode potential exceeds $+1.1$ V at 25° C. in a 15 wt.% aqueous sulfuric acid solution (based on a mercury sulfate electrode; $+1.7$ V, when expressed in a standard hydrogen electrode potential), a sudden decrease of the benzyl alcohol selectivity is observed in the reduction of any benzoic acids.

The inventors have thus found that it is desirable to conduct the reaction at an anode potential of not higher than $+1.1$ V in order to attain a high selectivity in a single electrolytic cell. However, in using anode materials inherently involving high oxygen overvoltages (not less than $+1.1$ V at a practical current density of from 0.1 A/dm$^2$ to 100 A/dm$^2$), such as platinum, lead oxide, lead and lead alloys, which are generally used stably in aqueous acidic solutions, if the electrolytic reaction is conducted in an aqueous acidic solution by maintaining the anode potential at as low as $+1.1$ V or less, the current density must be reduced to far less than 0.1 A/dm$^2$, resulting in a prolonged reaction time and a lowered efficiency of the electrolytic cell.

The inventors have also found that by using electrode materials having inherent oxygen overvoltages of $+1.1$ V or less at a practical current density for electrolytic reactions (commonly in the order of from 0.1 A/dm$^2$ to 100 A/dm$^2$) as the anode, it becomes possible to design an industrially practicable process using a single electrolytic cell in which the anode compartment is not separated from the cathode compartment.

In the electrolytic reaction in an aqueous acidic solution, oxygen generation due to the electrolysis of water and oxidation-decomposition of aromatic carboxylic acids used as the raw material and/or of organic compounds derived from the raw material takes places competitively at the anode. Then, use of an anode material of a low oxygen overvoltage allows the electrolysis of water at the anode to take place at a low potential so that oxygen generates there preferentially. Thus, it becomes possible to control the oxidation-decomposition of organic matters by the anode, which is responsible for the decrease in the yield of the intended benzyl alcohols. The invention has been completed on the basis of these findings.

The invention offers an electroreduction process of aromatic carboxylic acids which comprises, in the electroreduction of aromatic carboxylic acids in an aqueous acidic solution to produce the corresponding benzyl alcohols, conducting the reaction under the control of the oxidation-decomposition of organic matters by the use of an anode material involving a low oxygen overvoltage as the anode material for oxygen generation.

No particular limitations are placed on the aromatic carboxylic acids used as the raw material in the invention, so far as they are reducible in a conventional electrolytic cell consisting of two compartments in which a diaphragm is provided. They may include, for example, benzoic acid, hydroxybenzoic acid, alkoxybenzoic acids, phenoxybenzoic acid, aminobenzoic acid, alkylbenzoic acids, isophthalic acid and hydroxymethylbenzoic acid.

As the anode material involving a low oxygen overvoltage, which is useful in the practice of the invention, it is advisable to use a metallic oxide which is preferably stable in an aqueous acidic solution and the oxygen overvoltage of which is not higher than $+1.1$ V at a supply current density of from 0.1 A/dm$^2$ to 100 A/dm$^2$ on the basis of a mercury sulfate electrode (measured at 25° C. in a 15 wt.% aqueous sulfuric acid solution; not higher than $+1.7$ V, when expressed in a standard hydrogen electrode potential). The anode may also include a metallic substrate having its surface covered by the oxide.

As the oxide may be mentioned the oxides of Group VIII, platinum group, such as ruthenium oxide, rhodium oxide, palladium oxide, osmium oxide, iridium oxide, platinum oxide, tin oxide, tantalum oxide and cobalt oxide, and mixtures thereof.

It is preferable from an industrial viewpoint to use DSE (Dimensionally Stable Electrode) formed by coating the surface of a metallic titanium substrate with the oxide of a platinum group metal as the chief component.

In the invention, there is no particular restriction imposed on the aqueous acidic solution, so far as it is of an acidic substance inert to the electrolytic reaction at the cathode. However, mineral acids may preferably be used in view of cost. Among others, sulfuric acid is favorable from the standpoint of material and yield, and hence a 1 to 50 wt.% aqueous sulfuric acid is generally used.

It is also preferable in the invention to add a quaternary ammonium salt, an aprotic polar solvent or both of them into the electrolytic reaction solution, for the purpose of increasing the solubility of aromatic carboxylic acids used as the raw material.

The quaternary ammonium salt is represented by the formula (I):

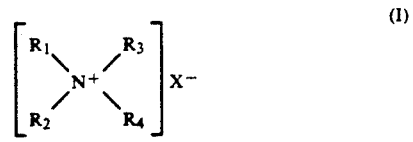

wherein $R_1$, $R_2$, $R_3$ and $R_4$ are individually a lower alkyl group and X represents the acid radical of p-toluenesulfonic acid, sulfuric acid, hydrochloric acid or hydrobromic acid. Among these ammonium salts are tetraethylammonium p-toluenesulfonate, tetramethylammonium p-toluenesulfonate, tetrapropylammonium p-toluenesulfonate, tetrabutylammonium p-toluenesulfonate, and the sulfates, chlorides and bromides substituted for these p-toluenesulfonates. These salts are added to the aqueous acidic solution in an amount up to a high of 60 wt.%.

The aprotic polar solvent may include acetonitrile, N,N'-dimethylimidazolidinone, N,N'-dimethylformamide, N-methyl-2-pyrrolidone and sulfolane. These polar solvents are added in an amount up to a high of 10 fold by weight based on the aqueous acidic solution used.

The concentration of the aromatic carboxylic acid in the aqueous acidic solution generally ranges from 1 wt.% to 40 wt.%.

In the invention, the electroreduction is carried out at a temperature in the range of from 20° C. to 100° C. Of the electrodes for use in the electrolysis, the cathode employs a material involving a high hydrogen overvoltage, specifically, zinc, lead, cadmium or mercury.

In the electroreduction of the invention, the current density may preferably be in the range of from 1 A/dm$^2$ to 30 A/dm$^2$. Theoretically, the reaction entails 4-electron reduction so that it could have been accomplished by a quantity of electricity of 4 Fr/mol. However, a quantity of electricity of from 8 Fr/mol to 20 Fr/mol is required to complete the reaction, because the current efficiency is about 20% to 80%.

No particular limitation is imposed on the electrolytic apparatus used in the invention. Basically, however, it is usual to employ a method comprising charging an electrolyte (2) in a beaker-type electrolytic cell (1) in which no diaphragm is provided, fixing an anode (3) and a cathode (4) therein and conducting a current therethrough from a DC power supply (see FIG. 1).

Figure 2:
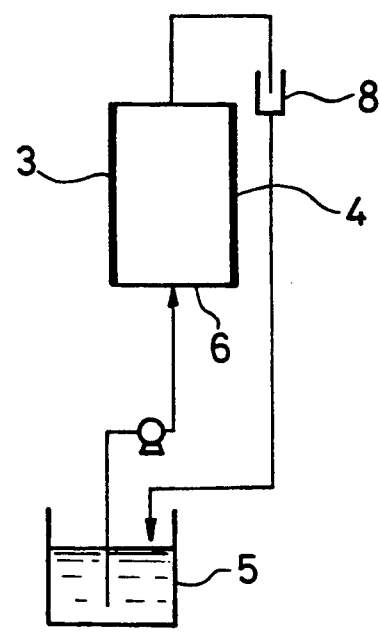
FIG. 2 is similarly a schematic cross section of the filter press-type single electrolytic apparatus.

In the case of a filter press-type electrolytic apparatus, it is feasible to use a single electrolytic apparatus in which both of the anode-cathode electrolytic chamber and a solution tank (5) are not divided, as seen in FIG. 2.

Further, upon the electrolytic reaction in an aqueous solution, oxygen evolves at the anode on account of the electrolysis of water, whereas at the cathode, hydrogen generation occurs by the electrolysis of water as a side reaction, in addition to the reduction of a benzoic acid used as the raw material. Thus, there is a danger of explosion due to the mixing of oxygen and hydrogen.

As a means to avoid the danger of explosion, it is preferable, for example, to blow forcibly an inert gas like nitrogen or argon into the electrolytic cell (1) or the electrolytic chamber (6) and a gas-liquid separator (8), reduce the pressure in the electrolytic call or chamber, and withdraw the gases to the outside of the system effectively.

Figure 4:
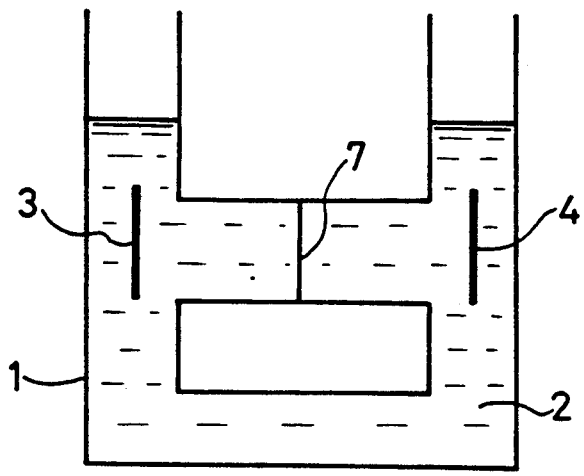
FIG. 4 is a schematic cross section of the vessel-type single apparatus of the invention in which a diaphragm is provided only between the anode and the cathode.
Figure 5:
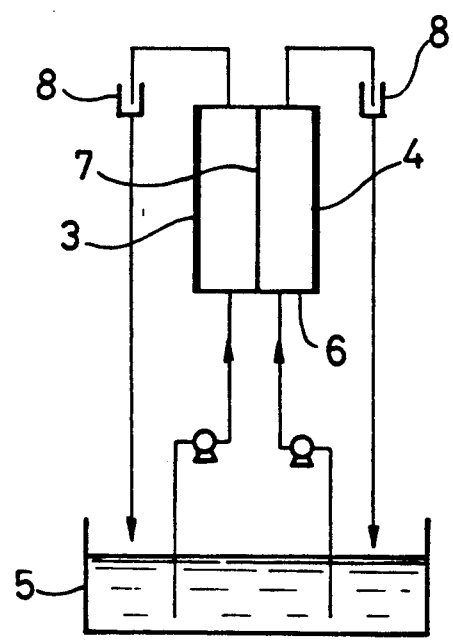
FIG. 5 is similarly a schematic cross section of the filter press-type electrolytic apparatus.

It is also possible to use a process in which hydrogen and oxygen in the electrolytic cell or chamber are diluted so that the reaction can be carried out under the lower explosion limit of hydrogen, an apparatus as illustrated in FIG. 4 in which the electrolytic cell itself is not divided but a diaphragm (7) is provided in the section involving the danger of the mixing of the generated gases with a view toward the prevention of the mixing of oxygen and hydrogen, and a filter press-type single apparatus as shown in FIG. 5 in which one solution tank is not divided and a diaphragm is provided only in the electrolytic chamber to isolate the two gases.

In the electroreduction of aromatic carboxylic acids, when the reaction is carried out in an anode-cathode separated electrolytic apparatus, a cation-exchange membrane is commonly used as a diaphragm so as to minimize the transfer of organic matters from the cathode to the anode and, in addition, to make smooth the transfer of protons from the anode to the cathode, with the aim of improving the rate of recovery of the intended products in the cathode compartment. However, the cation exchange membrane is expensive and entails the problem of instability in long-term operations.

However, in the case of the diaphragm useful in the practice of the invention, it is not necessary to consider the transfer of organic matters from the cathode to the anode and that of protons from the anode to the cathode. Therefore, it is possible to use neutral polymer membranes, asbestos diaphragms, glass diaphragms, etc. which are inexpensive and stable as well as are capable of separation of the generated gases at the anode and cathode.

The invention is illustrated specifically by reference to the following examples. In the examples, "%" signifies wt.%. The oxygen overvoltage of the anode was measured at 25° C. in a 15 wt.% aqueous sulfuric acid by the use of a mercury sulfate electrode as a reference electrode.

EXAMPLE 1

In a 100-ml cylindrical single electrolytic cell were charged 25 g of a 15 wt.% aqueous sulfuric acid and 1 g of m-hydroxybenzoic acid. A 6-cm$^2$ lead plate and a 6-cm$^2$ titanium plate having its surface coated with iridium oxide (oxygen overvoltage: +0.95 V vs Hg$_2$SO$_4$) were used as a cathode and an anode, respectively.

While maintaining the electrolytic cell at 50° C., 1 A of a constant DC was allowed to flow for 2 hours (10.3 Fr/mol).

Thereafter, the reaction solution was analyzed by liquid chromatography (HPLC). The analysis revealed that the rate of residual m-hydroxybenzoic acid was 2.5% and the yield of m-hydroxybenzyl alcohol was 86.9%, based on the feed m-hydroxybenzoic acid (current efficiency: 37.9%).

EXAMPLE 2

An experiment was conducted in much the same manner as in Example 1, except that a titanium plate coated with iridium oxide and tantalum oxide (oxygen overvoltage: +0.88 V vs Hg$_2$SO$_4$) was used as the anode in place of the titanium plate coated with iridium oxide.

The reaction solution was analyzed by HPLC. The rate of residual m-hydroxybenzoic acid was found to be 2.1%, while the yield of m-hydroxybenzyl alcohol was 88.5%, based on the feed m-hydroxybenzoic acid (current efficiency: 38.0%).

EXAMPLE 3

An experiment was conducted in much the same manner as in Example 1, except for the use of 0.88 g of benzoic acid in place of the m-hydroxybenzoic acid as the reaction raw material.

The reaction solution was analyzed by HPLC. The analysis revealed that the rate of residual benzoic acid was 0.9% and the yield of benzyl alcohol was 91.5%, based on the feed benzoic acid (current efficiency: 38.5%).

EXAMPLE 4

An experiment was conducted in much the same manner as in Example 1, except that 0.78 g of m-phenoxybenzoic acid was used in place of the m-hydroxybenzoic acid as the reaction raw material, 1 g of tetraethylammonium p-toluenesulfonate being added, and 1 A of a constant DC was allowed to flow for 1.5 hours (15.4 Fr/mol).

The reaction solution was analyzed by HPLC. The analysis revealed that the rate of residual m-phenoxybenzoic acid was 1.1% and the yield of m-phenoxybenzyl alcohol was 90.5%, based on the feed m-phenoxybenzoic acid (current efficiency: 25.7%).

EXAMPLE 5

An experiment was conducted in much the same manner as in Example 1, except for the use of 0.99 g of o-aminobenzoic acid in place of the m-hydroxybenzoic acid as the reaction raw material.

The reaction solution was analyzed by HPLC. The analysis revealed that the rate of residual o-aminobenzoic acid was 0.5% and the yield of o-aminobenzyl alcohol was 81.2%, based on the feed o-aminobenzoic acid (current efficiency: 38.6%).

EXAMPLE 6

An experiment was conducted in much the same manner as in Example 1, except that 1.54 g of 2,3,4-trimethoxybenzoic acid was used in place of the m-hydroxybenzoic acid as the reaction raw material and 5 g of acetonitrile was added.

The reaction solution was analyzed by HPLC. The analysis revealed that the rate of residual 2,3,4-trimethoxybenzoic acid was 5.2% and the yield of 2,3,4-trimethoxybenzyl alcohol was 82.6%, based on the feed 2,3,4-trimethoxybenzoic acid (current efficiency: 36.8%).

EXAMPLE 7

In a filter press-type single electrolytic apparatus equipped with a 300-ml solution tank as shown in FIG. 5 were charged 250 g of a 15 wt.% aqueous sulfuric acid and 10 g of m-hydroxybenzoic acid.

A lead plate with an effective area of 50 cm² and a titanium plate with an effective area of 50 cm² which is coated on its surface with iridium oxide (oxygen overvoltage: +0.88 V vs Hg$_2$SO$_4$) were used as a cathode and an anode, respectively. Between the two electrodes, an asbestos diaphragm was provided to prevent the generated gases at the electrodes from mixing.

While maintaining the electrolytic cell at 50° C., 5 A of a constant DC was allowed to flow for 4 hours (10.3 Fr/mol).

Thereafter, the reaction solution was analyzed by liquid chromatography (HPLC). The analysis revealed that the rate of residual m-hydroxybenzoic acid was 2.0% and the yield of m-hydroxybenzyl alcohol was 88.6%, based on the feed m-hydroxybenzoic acid (current efficiency: 38.0%).

COMPARATIVE EXAMPLE 1

An experiment was conducted in much the same manner as in Example 1, except for the use of a platinum plate (oxygen overvoltage: +1.3 V vs Hg$_2$SO$_4$) in place of the iridium oxide as the anode.

The reaction solution was analyzed by HPLC. The analysis revealed that the rate of residual m-hydroxybenzoic acid was 0.2% and the yield of m-hydroxybenzyl alcohol was 17.2%, based on the feed m-hydroxybenzoic acid.

COMPARATIVE EXAMPLE 2

An experiment was conducted in much the same manner as in Example 1, except for the use of a lead plate (oxygen overvoltage: +1.4 V vs Hg$_2$SO$_4$) in place of the iridium oxide as the anode.

The reaction solution was analyzed by HPLC. The analysis revealed that the rate of residual m-hydroxybenzoic acid was 0.6% and the yield of m-hydroxybenzyl alcohol was 5.9%, based on the feed m-hydroxybenzoic acid.

COMPARATIVE EXAMPLE 3

An experiment was conducted in much the same manner as in Comparative Example 1, except for the use of 0.78 g of benzoic acid in place of the m-hydroxybenzoic acid as the reaction raw material.

The reaction solution was analyzed by HPLC. The analysis revealed that the rate of residual benzoic acid was 1.2% and the yield of benzyl alcohol was 26.2%, based on the feed benzoic acid.

REFERENCE EXAMPLE

Using a H-type electrolytic cell which is divided into two electrolytic chambers, each having a volume of 100 ml, by a diaphragm called Celemion CMV (trade name; a cation exchange membrane manufactured by Asahi Glass Co.), 50 g of a 15% aqueous sulfuric acid was charged in each of the chambers. A 6-cm² lead plate and a 6-cm² platinum plate (oxygen overvoltage: +1.3 V vs Hg$_2$SO$_4$) were used as a cathode and an anode, respectively.

While maintaining the electrolytic cell at 50° C., 2 g of m-hydroxybenzoic acid was charged in the cathode chamber and 1 A of a constant DC was allowed to flow for 4 hours (10.3 Fr/mol).

The cathode solution was analyzed by HPLC. The analysis revealed that the residual rate of the feed m-hydroxybenzoic acid was 2.3% and the yield of m-hydroxybenzyl alcohol was 83.0% (current efficiency: 37.9%).

What is claimed is:

1. In a process for the production of a benzyl alcohol by the electroreduction of a corresponding aromatic carboxylic acid in an aqueous acidic solution in an electrolytic cell at a supply current density of from 0.1 A/dm² to 100 A/dm², the improvement which comprises the combination of conducting the reduction in a diaphragm-less cell and using an anode material involving an oxygen overvoltage of not more than +1.1 V vs Hg$_2$SO$_4$ at 25° C. in a 15 wt. % aqueous sulfuric acid solution at the supply current density employed (not more than +1.7 V, when expressed in a standard hydrogen electrode potential), the anode material for oxygen generation thereby producing the corresponding benzyl alcohol in a yield comparable to that achievable in a diaphragmed cell by avoiding the concurrent reoxidation thereof.

2. The process as claimed in claim 1 wherein the anode material is a metallic oxide stable in the aqueous acidic solution.

3. The process as claimed in claim 2 wherein the metallic oxide is selected from the group consisting of ruthenium oxide, rhodium oxide, palladium oxide, osmium oxide, iridium oxide, platinum oxide, tin oxide, tantalum oxide and cobalt oxide and mixtures thereof.

4. The process as claimed in claim 1 wherein the aqueous acidic solution is an aqueous solution of a mineral acid.

5. The process as claimed in claim 4 wherein the mineral acid is sulfuric acid.

6. The process as claimed in sulfate electrode claim 5 wherein the concentration of the sulfuric acid is in the range of from 1 wt.% to 50 wt.%.

7. The process as claimed in claim 1 wherein the electrolytic reaction solution contains at least either a quaternary ammonium salt or an aprotic polar solvent.

8. The process as claimed in claim 7 wherein the quaternary ammonium salt is an ammonium salt represented by the formula (I):

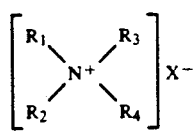

wherein $R_1$, $R_2$, $R_3$ and $R_4$ are individually a lower alkyl group and X represents the acid radical of p-toluenesulfonic acid, sulfuric acid, hydrochloric acid or hydrobromic acid.

9. The process as claimed in claim 7 wherein the ammonium salt is contained in the aqueous acidic solution in an amount up to 60 wt.%.

10. The process as claimed in claim 1 wherein the concentration of the aromatic carboxylic acid in the aqueous acidic solution is in the range of from 1 wt.% to 40 wt.%.

11. The process as claimed in claim 1 wherein the electroreduction is conducted at a current density of from 1 A/dm$^2$ to 30 A/dm$^2$.

12. The process as claimed in claim 1 wherein the electroreduction is carried out batchwise.

13. The process as claimed in claim 1 wherein the electrolytic cell is of a filter press-type.

14. The process as claimed in claim 1 wherein the electroreduction is conducted under the introduction of an inert gas.

15. The process as claimed in claim 1 wherein the electroreduction is conducted in a cell provided with a diaphragm for preventing the generated gases from mixing.

16. The process as claimed in claim 15 wherein the diaphragm is a filter membrane.

17. The process as claimed in claim 16 wherein the filter membrane is a neutral polymer membrane.

18. The process as claimed in claim 16 wherein the filter membrane is an asbestos diaphragm.

19. The process as claimed in claim 16 wherein the filter membrane is a glass diaphragm.

* * * * *